Figure 1:
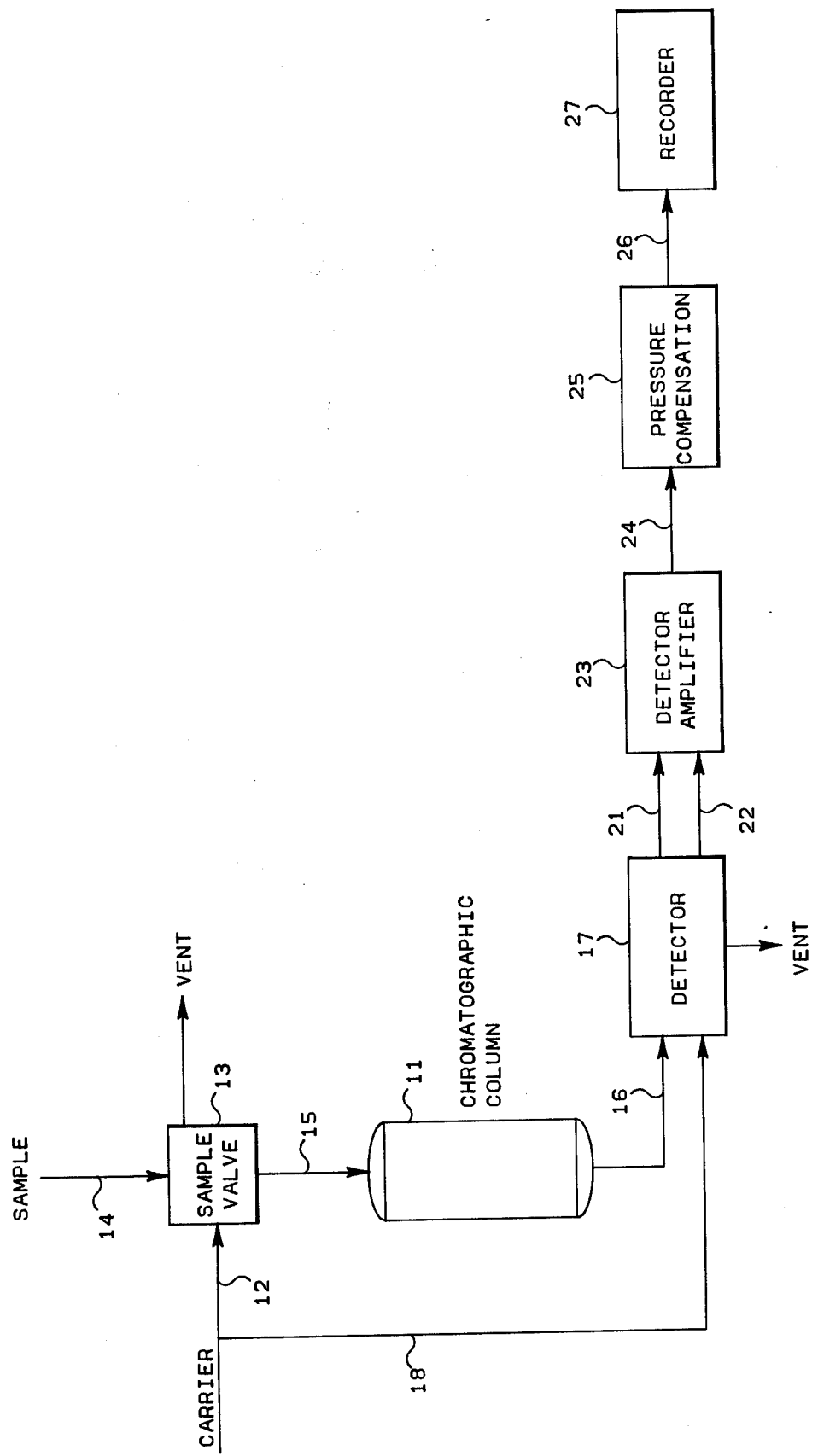

United States Patent [19]

DeFord et al.

[11] 4,141,237

[45] Feb. 27, 1979

[54] PRESSURE COMPENSATION METHOD AND APPARATUS FOR A CHROMATOGRAPH

[75] Inventors: Donald D. DeFord, Evanston, Ill.; Edwin K. Clardy, Bartlesville, Okla.

[73] Assignee: Phillips Petroleum Company, Bartlesville, Okla.

[21] Appl. No.: 880,923

[22] Filed: Feb. 24, 1978

[51] Int. Cl.$^2$ ............................................. G01N 31/08
[52] U.S. Cl. ..................................................... 73/23.1
[58] Field of Search .............................. 73/23.1, 27 R; 23/232 C, 254 R

[56] References Cited

U.S. PATENT DOCUMENTS 3,240,052  3/1966  Reinecke et al. ..................... 73/23.1
3,283,563  11/1966  Turner et al. ......................... 73/23.1

Primary Examiner—Stephen A. Kreitman

[57] ABSTRACT

A method and apparatus is disclosed for correcting errors in a chromatographic analysis caused by changes in ambient atmospheric pressure. The output signal from a chromatograph is summed with the output signal from a pressure transducer. The output signal from the pressure transducer varies with changes in the atmospheric pressure from a reference pressure and is calibrated in such a manner as to provide a corrected chromatographic analyzer output signal when it is summed with the output signal from the chromatograph. In this manner pressure compensation is provided where normalization of the chromatographic analyzer output signal is not possible or is undesirable.

16 Claims, 2 Drawing Figures

PRESSURE COMPENSATION METHOD AND APPARATUS FOR A CHROMATOGRAPH

This invention relates to chromatography. In a particular aspect this invention relates to method and apparatus for correcting errors in a sample analysis caused by barometric pressure variations.

A chromatograph is an analytical instrument that is used to individually detect the constituents of a sample to be analyzed. The chromatograph typically includes an analytical column through which a carrier fluid is passed continuously. The sample to be analyzed is injected into the carrier stream and is thus carried through the analytical column. The sample constituents are absorbed on the packing material in the analytical column at different affinities and are eluted from the column at different points in time.

A detector is employed to detect the separated constituents and the detector output signal can be plotted as a function of time to produce what is termed a chromatogram. As each sample component is eluted from the column it produces a sharp increase in the detector output signal amplitude which appears as a peak or spike in the chromatogram.

Small errors in the sample component analysis may result from changes in ambient atmospheric pressure in the immediate area of the chromatographic system. In many systems, if a sample valve is used to measure a definite volume of sample and to inject the sample into the carrier fluid, a change in ambient atmospheric pressure (barometric pressure) influences the mass of the sample taken for analysis because the sample in the sample valve is at a pressure which is a function of atmospheric pressure. A change in ambient atmospheric pressure will also influence the height and area of the peaks which are representative of the sample components because the carrier velocity at the column outlet is also dependent on atmospheric pressure.

It is a common practice to correct any errors that may result from changes in ambient atmospheric pressure by normalizing the chromatograph output. The area of the output peak resulting from each individual component is divided by the total area of all peaks to normalize the chromatograph output and in this manner errors caused by changes in ambient atmospheric pressure are corrected. However, normalization of the output of a chromatograph is often time consuming and sometimes cannot be performed. A total analysis of all the components of the sample is usually required before normalization of the peak signals can be carried out. When only two or three components of a sample having many more components are to be analyzed, a compensation for atmospheric pressure variations can be more desirable than normalization of the chromatograph output. Compensation for atmospheric pressure variations may also be desirable where the analysis must be performed in a short length of time.

Accordingly, it is an object of this invention to provide method and apparatus for correcting errors in a sample analysis caused by barometric pressure variations.

In accordance with the present invention, method and apparatus is provided whereby the output of the detector, which is normally supplied to a recorder, computer, or control instrument, is supplied to a summing means. A pressure transducer is utilized to provide a signal which is representative of atmospheric pressure. The signal from the pressure transducer is also supplied to the summing means. Changes in atmospheric pressure result in changes in the signal from the pressure transducer. A simple calibration makes it possible to correct any errors that may result from changes in atmospheric pressure by simply summing the output of the pressure transducer and detector in the summing means. In this manner a correct chromatograph output is provided from the output of the summing means to recorder, computer, or some control instrument.

Figure 2:
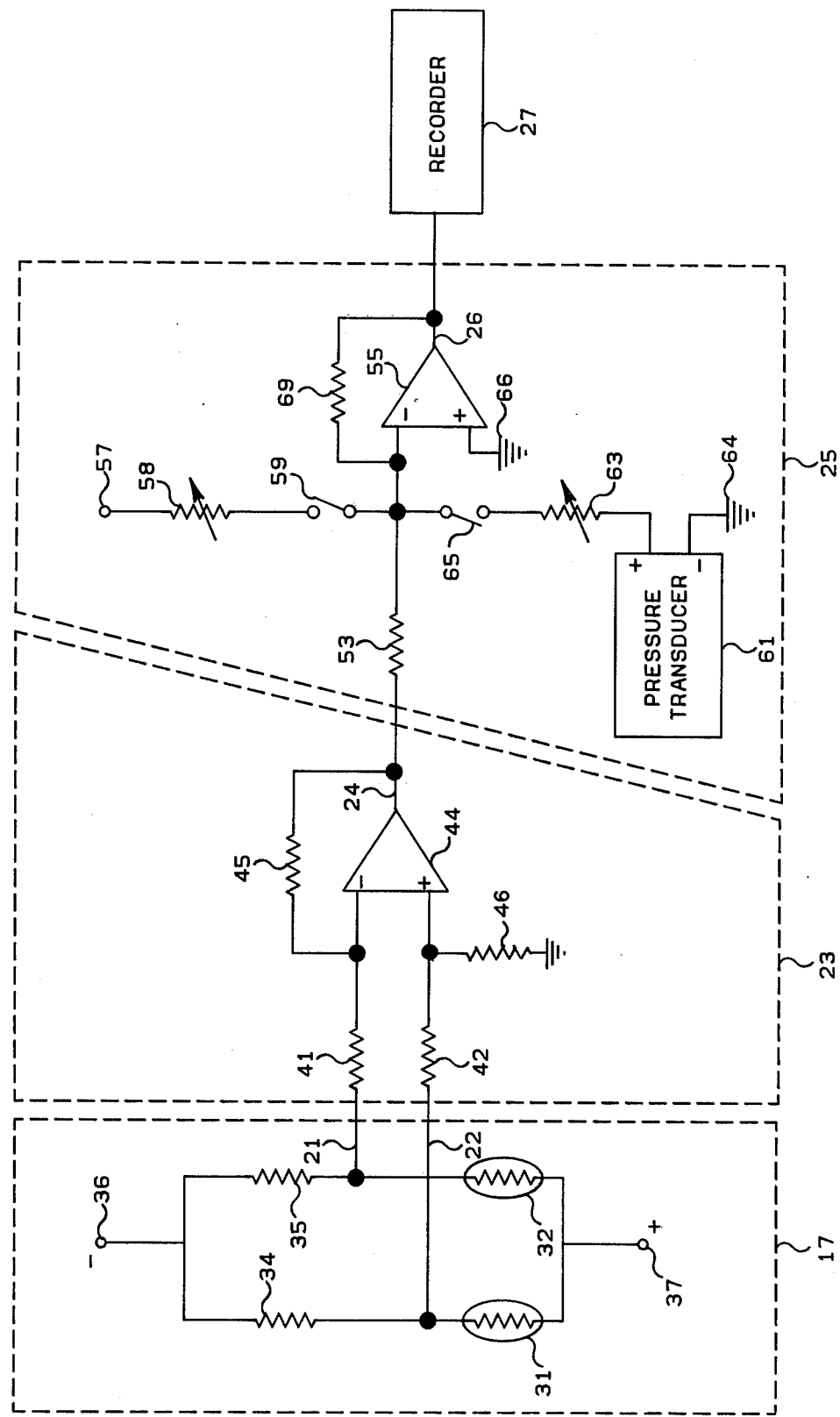

Other objects and advantages of the invention will be apparent from the following description of the invention as illustrated by the drawings in which:

FIG. 1 is an illustration of a chromatographic analysis system with pressure compensation added; and FIG. 2 is a schematic of the detector, detector amplifier and pressure compensation system shown in FIG. 1.

The invention is described in terms of a typical chromatographic analysis system where a sample valve is utilized and the output is provided to a recorder. The invention is, however, not limited to this configuration but is applicable to any chromatographic analyzer configuration where pressure compensation is desired. The invention is also described in terms of electrical signals but is applicable to other types of signals such as pneumatic.

As used in this disclosure the term pressure refers to absolute pressure.

Although it is necessary in the most general case to multiply the measured peak height or peak area by a factor that is a function of the ambient atmospheric pressure in order to obtain a corrected, pressure-independent area, this correction can be applied by simple addition of a signal that is proportional to pressure if the composition of the sample varies only slightly from one sample to another. This invention is thus described in terms of a sample which varies only slightly from sample to sample; thus, a simple addition is used in the preferred embodiment of the invention. The invention is, however, applicable to those situations where sample size varies appreciably from sample to sample and multiplication is required.

Referring now to the drawing and in particular to FIG. 1, there is shown a chromatographic column 11. A carrier fluid is introduced through conduit means 12 into sample valve 13. A sample of a fluid to be analyzed is delivered to sample valve 13 through conduit means 14. A conduit means 15 extends between sample valve 13 and the inlet to chromatographic column 11. A conduit means 16 extends between the outlet of chromatographic column 11 and the first inlet of a detector means 17. Carrier fluid is passed through the reference portion of detector means 17 by being introduced into the second inlet of detector means 17 through conduit means 18 which communicates with conduit means 12. Carrier fluid also flows through sample valve 13 and chromatographic column 11 to the fluid inlet of detector means 17.

At the beginning of an analysis period, sample valve 3 is actuated to introduce a predetermined volume of sample into the carrier fluid flowing through chromatographic column 11. The constituents of the sample are eluted in sequence and flow from chromatographic column 11 through conduit means 16 to the sample portion of detector means 17.

Detector means 17 establishes a differential output by establishing an electrical signal 21 representative of the composition of the carrier fluid carrying the sample passing through the sample portion of detector means 17 and an electrical signal 22 representative of the composition of the carrier fluid only in the reference portion of detector means 17. Signals 21 and 22 are then compared by detector amplifier 23 to produce signal 24 representative of a chromatographic analyzer output signal. Signal 24 is supplied to the pressure compensation system 25. The pressure compensation system 25 operates on signal 24 to produce signal 26 which is representative of the atmospheric pressure compensated chromatographic analyzer output signal. In this preferred embodiment signal 26 is supplied to recording means 27 where it is stored.

FIG. 2 illustrates a preferred embodiment of the detector means 17, the detector amplifier 23, and the pressure compensation system 25 illustrated in FIG. 1. The detector means 17 is a thermal conductivity detector in this preferred embodiment. Other types of detectors, such as flame ionization detectors, could also be utilized. Detector means 17 is provided with thermistors 31 and 32. Thermistor 31 is located in the stream of carrier fluid which carries the sample and is termed a sense thermistor. Thermistor 32 is located in the reference stream of the carrier fluid and is termed a reference thermistor. The thermistors 31 and 32 are wired in a bridge circuit with resistors 34 and 35. A constant voltage is supplied across the bridge circuit by power supplies 36 and 37. Heat is supplied to thermistors 31 and 32 by current passing through the thermistors. The generated heat is carried away by the fluid flowing past the thermistors. If the eluted components from the chromatographic column 11, shown in FIG. 1, have different thermal conductivities than the carrier fluid, the temperature 31 will vary with the type and quantity of each eluted component. This variation in temperature will result in unbalance in the bridge circuit and the voltage levels of signals 21 and 22 from the bridge circuit 36 will vary with respect to each other. Signal 21, which is representative of the sense element thermistor 31 output, is provided through resistor 41 to the inverting input of operational amplifier 44. Signal 22, which is representative of the reference element thermistor 32 output, is provided through resistor 42 to the noninverting input of operational amplifier 44. The noninverting input of operational amplifier 44 is also tied to ground through resistor 46. The output signal 24 from operational amplifier 44 is fed back through resistor 45 to the inverting terminal of operational amplifier 44. Signal 24, which is representative of the chromatographic analyzer output, is also supplied through resistor 53 to the inverting input of operational amplifier 55. The power supply 57 is tied to the inverting terminal of operational amplifier 55 through the variable resistor 58 and switching means 59. The positive input of the pressure transducer 61, which in this preferred embodiment is a GS-47 pressure transducer manufactured by Gulton Industries, is tied through variable resistor 63 and switching means 65 to the inverting input of operational amplifier 55. The negative input of the pressure transducer 61 is tied to ground 64. The noninverting input of operational amplifier 55 is also tied to ground 66. The output signal 26 from operational amplifier 55, which is representative of the pressure compensated chromatographic analyzer output, is fed back through resistor 69 to the inverting terminal of operational amplifier 55. Signal 26 is also supplied to recorder means 27 as is illustrated in FIG. 1.

As has been previously stated, small errors may be present in the detector amplifier 23 output signal 24 as a result of changes in the ambient atmospheric pressure. The actual magnitude and sign of the error is dependent on the type of detector 17 used and whether peak height or peak area is being measured. It is thus necessary to calibrate the pressure compensation system 25 for each particular chromatographic analyzer configuration and analysis method.

To calibrate the pressure compensation system 25, switching means 59 and 65 are opened and a known sample is analyzed by the chromatograph to produce an output signal 26 which is recorded. The atmospheric pressure at which the known sample was run is also noted.

After the results of the first run of the known sample have been recorded, switching means 59 and 65 are closed and the sample is run for a second time. The second run is made when the atmospheric pressure is different from that which existed when the first run was made. The variable resistors 58 and 63 are then manipulated until the output signal 26 which results from the second run is equal to the recorded output signal which resulted from the first run. The one-time setting of the variable resistors 58 and 63 is sufficient to calibrate the pressure compensation system 25 for all normal pressure variations. Samples can be run through the chromatographic analyzer after the variable resistors 58 and 63 are set, in the manner described above, and the pressure compensation system will automatically compensate for any errors caused by variations in atmospheric pressure.

The reference voltage which is supplied by power supply 57 is set so as to be equal to the output voltage from the pressure transducer 61 when the ambient atmospheric pressure is equal to one standard atmosphere (760 mm of Hg). The variable resistors 58 and 63 are always set to the same values; thus, no correction is applied when the ambient atmospheric pressure is equal to one standard atmosphere. As atmospheric pressure changes, the output voltage of the pressure transducer 61 will change resulting in a correction factor being added to or subtracted from the output signal 24 from the detector amplifier 23, depending on whether the atmospheric pressure is below or above one standard atmosphere.

The simplicity of this method is made possible by the fact that corrections for atmospheric pressure are small ($\pm$ 3% for normal extremes of atmospheric pressure). However, pressure compensation, even though small, can result in considerable savings where the chromatographic analysis of a product determines the value of the product. An example of this is where the BTU value of a heating fuel is determined by chromtographic analysis and the BTU value determines the price paid for the heating fuel.

The invention has been described in terms of its presently preferred embodiment as is shown in FIGS. 1 and 2. For the sake of convenience, signals which supply power to the operational amplifiers and the pressure transducer shown in the schematic of FIG. 2 have been omitted. Voltage levels required by the operational amplifiers and the pressure transducer are specified by the manufacturer and are well known to those familiar with the art.

Many different circuit configurations are possible which would perform the function required of the circuit shown in FIG. 2. FIG. 2 is illustrative of a particular circuit configuration which will perform the required functions.

Specific components which are available commercially and which can be used in the practice of the invention as shown in FIG. 2 follow. Values of resistors used in the circuit are also given. Again, many different combinations of circuit values, particularly in the area of resistance values, are possible.

| Thermistors 31 and 32 | AX 1775 (8K-Pair, Matched) Veco, Inc., Springfield, N.J. |
|---|---|
| Resistors 34 and 35 | 2.4K ± 1% W.W. Dale, Type RS-1B |
| Resistors 41 and 42 | 2.35 KΩ RN55D TRW/IRC |
| Resistor 45 | 23.5 KΩ RN55D TRW/IRC |
| Resistors 53 and 69 | 10 KΩ RN55D TRW/IRC |
| Operational Amplifiers 44 and 55 | LM741, National Semiconductor |
| Pressure Transducer | GS-47, Gulton Industries Costa Mesa, California |
| Variable resistors 58 and 63 | 10K ± 10%, Bourns, Model 3279W |

While the invention has been described in terms of the presently preferred embodiments, reasonable variations and modifications are possible by those skilled in the art, within the scope of the described invention and the appended claims.

That which is claimed is:

1. In a chromatograph system for analyzing the composition of a sample, said chromatograph system having a separating column and a detector means for providing an output signal having an amplitude which varies in accordance with the sample composition, the improvement comprising apparatus for compensating for errors in said output signal, said errors being produced by changes in the barometric pressure for the system, said apparatus comprising:
   means for generating a compensating signal which is representative of the effect on said output signal of the difference between the actual barometric pressure for the system and a reference pressure; and
   means for combining said output signal and said compensating signal in such a manner that errors, in said output signal, caused by changes in barometric pressure for the system are reduced.

2. Apparatus in accordance with claim 1 wherein said means for generating said compensating signal comprises:
   pressure transducer means for supplying a first signal which varies in response to changes in the barometric pressure with respect to a reference pressure;
   signal conditioning means for scaling said first signal to produce said compensating signal; and
   means for supplying said first signal to said signal conditioning means.

3. Apparatus in accordance with claim 2 wherein said signal conditioning means is a potentiometer.

4. Apparatus in accordance with claim 3 wherein said means for combining said output signal and said compensating signal is a summing amplifier means to which said output signal and said compensating signal are supplied.

5. Apparatus in accordance with claim 1 wherein said means for generating said compensating signal comprises:
   pressure transducer means for supplying a first signal which varies in response to changes in the barometric pressure for the system with respect to a reference pressure;
   first signal conditioning means for scaling said first signal to produce a second signal;
   means for supplying said first signal to said first signal conditioning means;
   means for supplying a reference signal;
   second signal conditioning means for scaling said reference signal to produce a third signal;
   means for supplying said reference signal to said second signal conditioning means; and
   means for combining said second signal and said third signal to produce said compensating signal.

6. Apparatus in accordance with claim 5 wherein said means for combining said second signal and said third signal comprises:
   a summing amplifier means;
   means for supplying said second signal to said summing amplifier means; and
   means for supplying said third signal to said summing amplifier means.

7. Apparatus in accordance with claim 6 wherein said means for combining said output signal and said compensating signal is said summing amplifier means to which both said second signal and said third signal are provided as inputs, said second signal and said third signal in combination forming said compensating signal, said output signal also being provided as as input to said summing amplifier means.

8. Apparatus in accordance with claim 5 wherein said means for combining said second signal and said third signal comprises:
   a summing amplifier means;
   a first switching means;
   a second switching means;
   means for supplying said second signal through said first switching means to said summing amplifier means; and
   means for supplying said third signal through said second switching means to said summing amplifier means.

9. Apparatus in accordance with claim 8 wherein said means for combining said output signal and said compensating signal is said summing amplifier means to which both said second signal and said third signal are provided as inputs, said second signal and said third signal in combination forming said compensating signal, said output signal also being provided as an input to said summing amplifier means.

10. Apparatus in accordance with claim 5 wherein said reference signal is equal to said first signal when the barometric pressure seen by said pressure transducer means is equal to one standard atmosphere and wherein said first signal conditioning scaling means is set equal to said second signal conditioning scaling means so that said compensating signal is equal to zero when the barometric pressure seen by said pressure transducer means is equal to one standard atmosphere.

11. Apparatus in accordance with claim 5 wherein said first and second signal conditioning scaling means are first and second potentiometers respectively.

12. In a method for analyzing the composition of a sample in a chromatographic system having a separating column and a detector for providing an output signal whose amplitude varies in accordance with sample composition, the improvement comprising compensating for errors in said output signal, said errors being produced by changes in the barometric pressure for the system by:

generating a compensating signal which is representative of the effect on said output signal of the difference between the actual barometric pressure for the system and a reference pressure; and combining said output signal and said compensating signal in such a manner that errors, in said output signal, caused by changes in barometric pressure for the system are reduced.

13. A method in accordance with claim 12 wherein said step of generating said compensating signal comprises:

generating a first signal which varies in response to changes in the barometric pressure for the system with respect to a reference pressure; and scaling said first signal to produce said compensating signal.

14. A method in accordance with claim 12 wherein said step of generating said compensating signal comprises:

generating a first signal which varies in response to changes in the barometric pressure for the system with respect to a reference pressure;

scaling said first signal to produce a second signal;

generating a reference signal;

scaling said reference signal to produce a third signal; and combining said second signal and said third signal to produce said compensating signal.

15. A method in accordance with claim 14 wherein said reference signal is set equal to said first signal when the barometric pressure for the system is equal to one standard atmosphere and wherein said scaling of said reference signal and said scaling of said first signal is equal so that said compensating signal is equal to zero when the barometric pressure for the system is equal to one standard atmosphere.

16. A method in accordance with claim 15 for calibrating said chromatograph system comprising the steps of:

disconnecting said compensating signal so that only said output signal is seen as an output of said chromatograph system;

analyzing a first sample in said chromatograph system to produce a fourth signal which is representative of the output signal from the chromatograph system which is not combined with said compensating signal, said analysis of said first sample being carried out at a first barometric pressure;

reconnecting said compensating signal so that said output signal will once again be combined with said compensating signal;

analyzing a second sample, which is substantially identical to said first sample, in said chromatograph system to produce a fifth signal, which is representative of said output signal combined with said compensating signal, the analysis of said second sample being carried out at a second barometric pressure which is different from said first barometric pressure; and scaling said first signal and said reference signal in such a manner that said first signal is equal to said fourth signal.

* * * * *

UNITED STATES PATENT AND TRADEMARK OFFICE
CERTIFICATE OF CORRECTION

PATENT NO. : 4,141,237
DATED : February 27, 1979
INVENTOR(S) : Donald D. DeFord and Edwin K. Clardy It is certified that error appears in the above-identified patent and that said Letters Patent are hereby corrected as shown below:

Column 6, claim 10, line 53, after "conditioning" delete "scaling".

Column 6, claim 10, line 54, after "conditioning" delete "scaling".

Column 6, claim 11, line 59, after "conditioning" delete "scaling".

Column 8, claim 16, line 30, after "said", first occurrence, delete "first" and insert therefor --- fifth ---.

Signed and Sealed this

Fourteenth Day of August 1979

[SEAL]

Attest:

LUTRELLE F. PARKER

*Attesting Officer*  *Acting Commissioner of Patents and Trademarks*